(12) United States Patent
Carbone

(10) Patent No.: US 8,142,396 B2
(45) Date of Patent: Mar. 27, 2012

(54) SYRINGE WITH RETRACTABLE NEEDLE

(75) Inventor: Carmelo Carbone, Avola (IT)

(73) Assignee: Amendola and Palmiateri (IT)

( * ) Notice: Subject to any disclaimer, the term of this patent is extended or adjusted under 35 U.S.C. 154(b) by 0 days.

(21) Appl. No.: 12/312,540

(22) PCT Filed: Nov. 14, 2007

(86) PCT No.: PCT/EP2007/062322
§ 371 (c)(1),
(2), (4) Date: May 15, 2009

(87) PCT Pub. No.: WO2008/058987
PCT Pub. Date: May 22, 2008

(65) Prior Publication Data
US 2010/0057002 A1    Mar. 4, 2010

(30) Foreign Application Priority Data

Nov. 15, 2006   (IT) .............................. MI2006A2190

(51) Int. Cl.
*A61M 5/00* (2006.01)
(52) U.S. Cl. ...................................... 604/110
(58) Field of Classification Search .................. 604/110, 604/192–198
See application file for complete search history.

(56) References Cited

U.S. PATENT DOCUMENTS

| | | | |
|---|---|---|---|
| 5,053,010 A | 10/1991 | McGary et al. | |
| 5,407,431 A | 4/1995 | Botich et al. | |
| 6,099,500 A | 8/2000 | Dysarz | |
| 6,228,054 B1 * | 5/2001 | Dysarz | 604/110 |
| 6,994,690 B2 * | 2/2006 | Kiehne | 604/110 |
| 7,014,622 B1 * | 3/2006 | Pressly et al. | 604/110 |
| 7,604,613 B2 * | 10/2009 | Crawford et al. | 604/110 |
| 2004/0116854 A1 | 6/2004 | Abulhaj et al. | |
| 2005/0159705 A1 | 7/2005 | Crawford et al. | |

FOREIGN PATENT DOCUMENTS

| | | |
|---|---|---|
| EP | 1092443 A2 | 4/2001 |
| WO | WO 2004/069315 A1 | 8/2004 |
| WO | WO 2005/004958 A1 | 1/2005 |

* cited by examiner

*Primary Examiner* — Matthew F Desanto
(74) *Attorney, Agent, or Firm* — H. Jay Spiegel

(57) ABSTRACT

There is described in a disposable syringe comprising: a syringe body, substantially comprising a hollow cylinder (1) with a plunger (2) -inserted therein, the plunger being hollow and closed at the end portion which is external to the cylinder, and a first plug (3) inserted in the plunger (2) end portion which is internal to the cylinder; -a needle body (4), substantially comprising a needle (5) having a pre-loaded spring (6) around the head (5') and a second plug (7) around the head of the needle, said spring determining the permanent introduction of said needle (5, 5') within said plunger (2) after use.

6 Claims, 3 Drawing Sheets

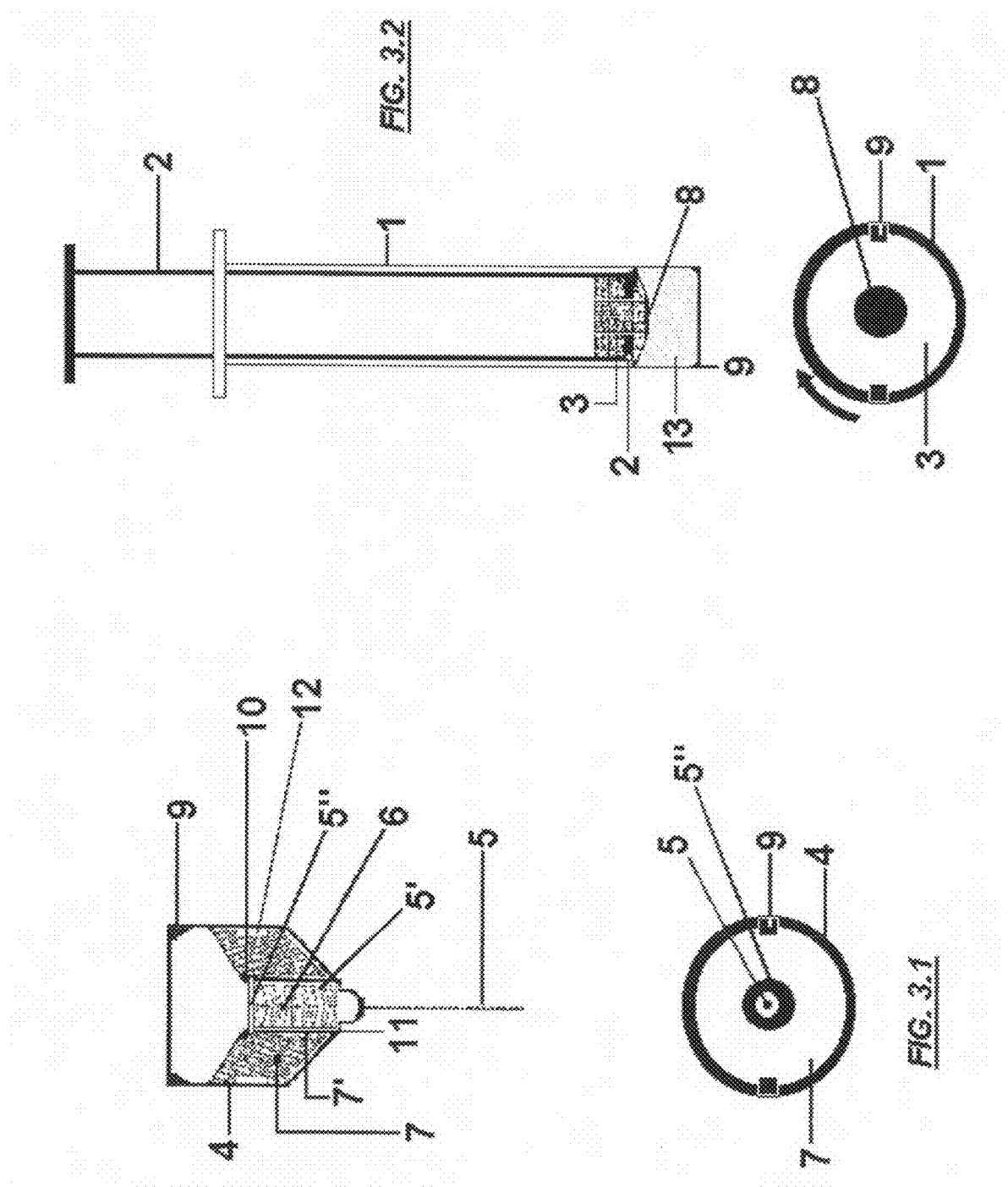

SYRINGE WITH RETRACTABLE NEEDLE

FIELD OF THE INVENTION

The present invention relates to a disposable syringe of the improved type.

Problems have long been known which concern the countless cases of infection due to the exchange of traditional syringes, for instance among drug addicts, or due to accidents caused by the puncture by needles of syringes which have been incautiously left on the ground, and may thus spread very serious diseases such AIDS, hepatitis and other infectious diseases.

DESCRIPTION OF RELATED ART

Disposable syringes of the traditional type do not solve this problem because the presence of the potentially contaminated and protruding needle still represents a danger in these terms.

Some attempts to solve this problem by providing disposable syringes having a needle which is retractable within the syringe itself after use, are known. However, these known kinds of disposable syringes have a complex structure, which displays a high number of components and results being expensive and difficult to use.

Therefore, it is the object of the present invention to overcome all of the aforesaid drawbacks and provide a disposable syringe of the improved type, which has an automatically retractable needle, a simple structure, a low production cost, is easy to use and consists of a limited number of parts.

SUMMARY OF THE INVENTION

The object of the present invention is a disposable syringe comprising: a syringe body, substantially comprising a hollow cylinder with a plunger inserted therein; the plunger being hollow and closed at the end portion which is external to the cylinder, and a first plug inserted in the plunger end portion which is internal to the cylinder; a needle body, substantially comprising a needle having a pre-loaded spring around the head and a second plug around the head of the needle, said spring determining the permanent introduction of said needle within said plunger after use.

A specific object of the present invention is a disposable syringe as described in better detail in the claims, which form an integral part of the present description.

BRIEF DESCRIPTION OF THE DRAWINGS

Further objects and advantages of the present invention will become apparent from the following detailed description of an embodiment thereof (and of variants thereof) and from the accompanying drawings given by way of mere non-limitative explanation, in which:

FIGS. 3.1 and 3.2 show a longitudinal section of a detailed exploded view of the two parts, respectively the needle body with a corresponding top view, and a syringe body with a corresponding bottom view, and with details of a type of connection.

DETAILED DESCRIPTION OF SPECIFIC EMBODIMENTS

Figure 1:
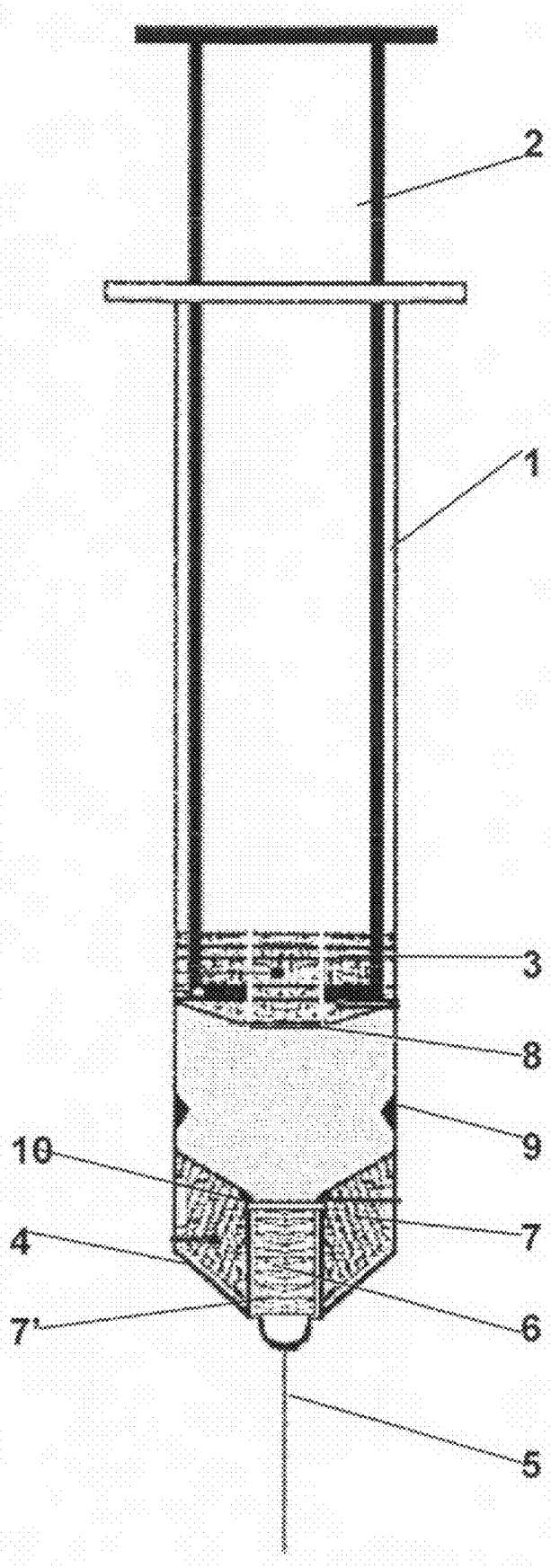
FIG. 1 shows a longitudinal section view of the ready-to-use disposable syringe which is the object of the present invention with the needle body inserted.

The same reference numbers and characters in the figures identify the same elements or components.

With reference to the figures, the disposable syringe is essentially formed by two detachable parts:
- a syringe body, essentially comprising a hollow cylinder 1 with a plunger 2 inserted therein, the plunger being hollow and closed at the end portion which is external to the cylinder, and a first plug 3 inserted in the plunger 2 end portion which is internal to the cylinder;
- a needle body 4, substantially comprising a needle 5 having a pre-loaded spring 6 around the head 5' and a second plug 7 around the head of the needle.

The first plug 3, made of a preformed rubber material, forms the seal of the plunger within the cylinder, and has an outer convex edge, and comprises a central semi-perforated part 8, at a central hole made in the plunger 2 end portion which is internal to the cylinder.

The needle body 4 is provided with means for the introduction and securing within the cylinder of the syringe, which for instance may comprise a bayonet 9 with fins or flarings of the male/female type, or a screwing or snap-fitting system.

The second plug 7, made of a preformed rubber material, has a concave edge facing towards the syringe body, the shape of which results being complementary to the convex shape of the first plug 3, and it comprises a central recess 7' to accommodate the head 5' of the needle 5.

The head 5' is provided with a widened upper edge 5" which, before use, engages against a rubber pad 10 within the recess of the plug 7 at the concave edge. The spring 6 engages on a narrowing 11 which is on the side opposite to the recess of the plug 7 and facing towards the point of the needle. It may be noted that the spring is pre-loaded between the upper edge 5" of the head of the needle and the narrowing 11 before use.

In use, the needle body is at first secured to the syringe body, and the syringe is ready for use.

Figure 2:
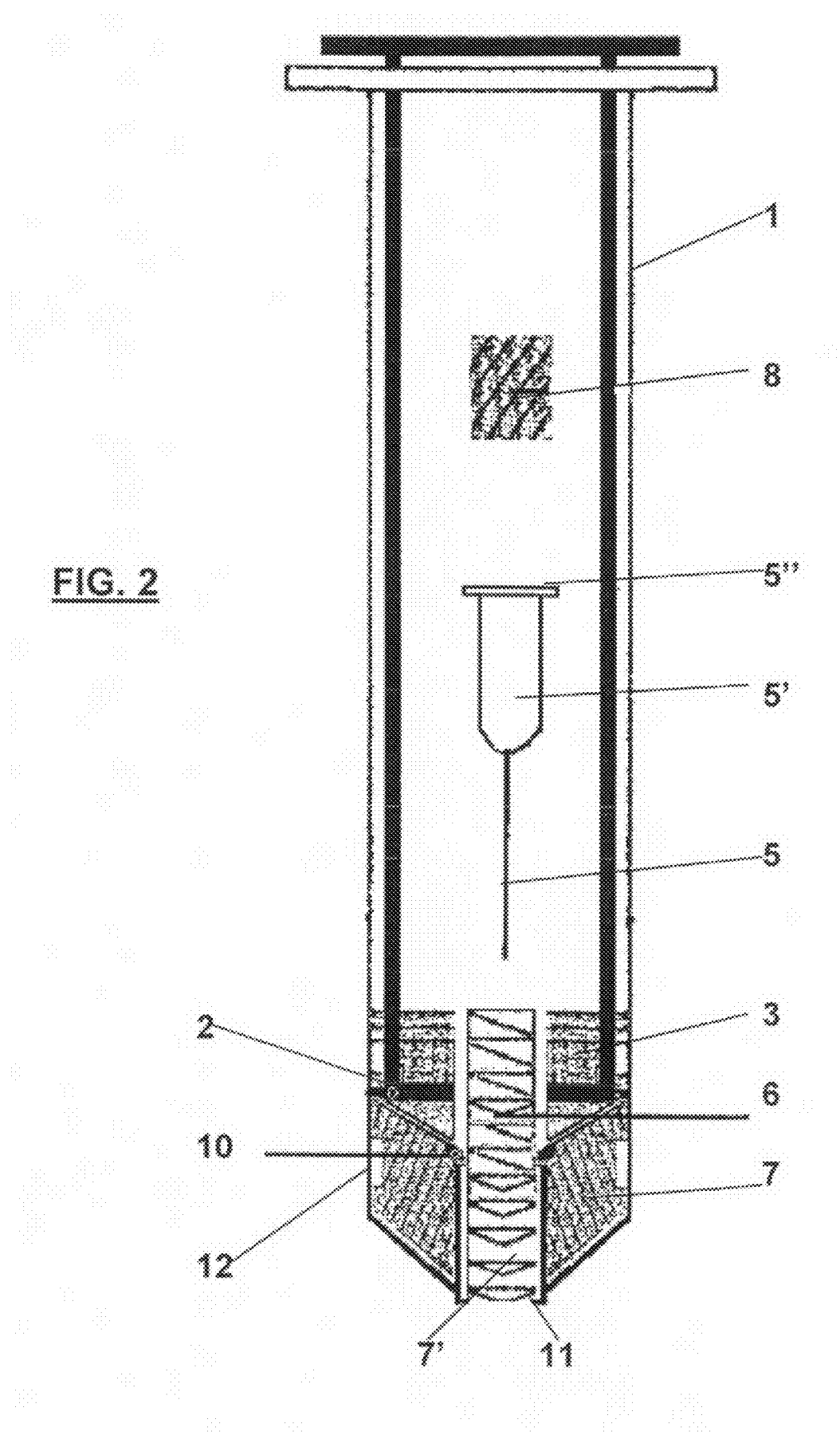
FIG. 2 shows a longitudinal section view of the disposable syringe which is the object of the present invention with the needle retracted within the cylinder after use.

After the injection of pharmacological liquid has been completed, the two concave and convex plugs 7 and 3 will come into contact (FIG. 2). In this position the internal edge of the plunger 2 will exert a pressure against the plug 7 leading the rubber pad 10 to widen (such a movement will also be possible in virtue of the two hollow areas 12 of the plug 7), the latter releasing the spring 6, which in turn will induce the head 5' of the needle 5 to pierce the previously perforated plug 3, and therefore permanently accommodate the entire needle within the plunger 2, together with the central semi-perforated part 8 of the plug 3.

Variants to the non-limitative embodiment described are possible without however departing from the scope of protection of the present invention, comprising all of the equivalent embodiments for a person skilled in the art.

The advantages resulting from the application of the present invention are apparent.

The ability of the needle to automatically and permanently self-retract within the plunger allows first of all to obtain a safe solution, by protecting from the common risks of infection and from the spreading of severe diseases such as AIDS, HEPATITIS and other infectious diseases, thus clearly ensuring the public health also in higher-risk environments such as hospitals, parks, beaches, etc. Furthermore, it allows to reduce the pain of a patient upon injection.

In this manner, the syringe may never again be used, thus allowing an extremely safe disposal, the potentially infectious part—consisting of the needle—being within the plunger.

The material used to make such a syringe will be the same product which is used for the manufacturing of already commercially available syringes.

The more significant elements of the disposable syringe according to the invention lead to a system which is simplified with respect to the similar traditional syringes and is innovative with respect to traditional disposable syringes, as they substantially consist of a plug and a spring, which are inserted in the needle body.

Pharmaceutical companies may achieve further advantages by using the upper part (cylinder) already filled with the drug 13 (FIG. 3.2). As the syringe is subdivided in two parts, the two parts only need to be connected by means of a bayonet connection for its use.

The body (provided with the needle, the plug and the loaded spring) will be ready for use, immediately after having been inserted on the cylinder, thus ensuring the ease of use and the maximum safety.

From the above description a person skilled in the art will be able to manufacture the object of the invention without introducing further constructive details.

The invention claimed is:

1. A disposable syringe comprising:
    a syringe body, substantially comprising a hollow cylinder with a plunger inserted therein, the plunger being hollow and closed at the end portion which is external to the cylinder, and a first plug inserted in the plunger end portion which is internal to the cylinder;
    a needle body, substantially comprising a needle having a pre-loaded spring around the head and a second plug around the head of the needle, said spring determining the permanent introduction of said needle within said plunger after use, said syringe body and said needle body being detachable;
    a central recess in the second plug, to accommodate the head of the needle, said head of the needle being provided with a widened upper edge;
    a rubber pad within the recess of the second plug, said rubber pad engaging against said widened upper edge of the head of the needle before use of the syringe;
    said first and second plugs coming into contact after use, so that the internal edge of the plunger exerts a pressure against the second plug leading the rubber pad to widen, the latter releasing the spring, which in turn induces the head of the needle to pierce the first plug, and therefore permanently accommodate the entire needle within the plunger, said first plug forming the seal of the plunger within the cylinder, and having an external convex edge, and comprising a central semi-perforated part, at a central hole located in the plunger end portion, which central hole is internal to the cylinder.

2. A disposable syringe according to claim 1, wherein said needle body is provided with means for insertion and securing within the cylinder of the syringe body.

3. A disposable syringe according to claim 2, wherein said means for the insertion and securing within the cylinder of the syringe body comprises a bayonet with fins or flarings of the male/female type, or a screwing or snap-fitting system.

4. A disposable syringe according to claim 1, wherein said second plug has a concave edge facing toward the syringe body, the shape of which is complementary to the convex shape of said first plug, and comprises a central recess to accommodate the head of the needle.

5. A disposable syringe according to claim 4, comprising a narrowing on a side opposite to the recess of said second plug and facing toward a distal point of the needle, said spring engaging on said narrowing; said spring being pre-loaded between the upper widened edge of the head of the needle and the narrowing before use.

6. A disposable syringe according to claim 1, wherein said central semi-perforated part permanently accommodates within the plunger, after the piercing of the first plug, together with the entire needle.

* * * * *